US012420046B2

(12) United States Patent
Shai (10) Patent No.: US 12,420,046 B2
(45) Date of Patent: Sep. 23, 2025

(54) NON-INVASIVELY AND SAFELY AND QUICKLY SURGICAL TECHNIQUE OF INSERTING T-SHAPED TUBE INTO STENOTIC TRACHEA

(71) Applicant: Taichung Veterans General Hospital, Taichung (TW)

(72) Inventor: Sen-Ei Shai, Taichung (TW)

(73) Assignee: TAICHUNG VETERANS GENERAL HOSPITAL, Taichung (TW)

( * ) Notice: Subject to any disclaimer, the term of this patent is extended or adjusted under 35 U.S.C. 154(b) by 907 days.

(21) Appl. No.: 17/590,240

(22) Filed: Feb. 1, 2022

(65) Prior Publication Data
US 2023/0241339 A1 Aug. 3, 2023

(51) Int. Cl.
*A61F 2/04* (2013.01)
*A61M 16/04* (2006.01)

(52) U.S. Cl.
CPC ........... *A61M 16/0472* (2013.01); *A61F 2/04* (2013.01); *A61M 16/0463* (2013.01); *A61F 2002/046* (2013.01)

(58) Field of Classification Search
CPC ........ A61F 2002/046; A61F 2230/0052; A61F 2/04; A61F 2/95; A61F 2/954; A61F 2005/4455; A61M 16/0472; A61M 2025/0079; A61M 25/0662; A61M 2039/0009; A61M 16/0463; A61B 2017/1135
USPC .......................... 606/153; 623/9; 128/207.29
See application file for complete search history.

(56) References Cited

U.S. PATENT DOCUMENTS

| 4,865,586 A * | 9/1989 | Hedberg ........... A61M 16/0463 64/35 |
| 6,210,429 B1 * | 4/2001 | Vardi ........................ A61F 2/82 606/198 |
| 7,182,771 B1 * | 2/2007 | Houser .................. A61B 17/11 623/1.36 |

(Continued)

FOREIGN PATENT DOCUMENTS

| CN | 107158536 A | * | 9/2017 |
| RU | 2410045 C1 | * | 1/2011 |
| WO | WO-2017216650 A1 | * | 12/2017 |

OTHER PUBLICATIONS

Abstract translation of RU 2410045 (Year: 2011).*

(Continued)

*Primary Examiner* — Brian E Pellegrino
(74) *Attorney, Agent, or Firm* — MUNCY, GEISSLER, OLDS & LOWE, P.C.

(57) ABSTRACT

A surgical technique, non-invasively and safely and quickly inserting a T-shaped tube into a stenotic trachea, is capable of replacing a traditional rigid bronchoscope with a harmless fiber bronchoscope dispense with additional surgical wound incision, utilization of an existing tracheostoma combined with the available guiding materials, the T-shaped tube can be readily inserted into the trachea; therefore, the surgical technique, non-invasively and safely and quickly inserting the T-shaped tube into the stenotic trachea elucidated in the invention is capable of safely and quickly manuvering patients with obvious subglottic stenosis to improve the prognosis without additional neck wound incision.

11 Claims, 5 Drawing Sheets

(56) References Cited

U.S. PATENT DOCUMENTS

2016/0128852 A1* 5/2016 Leanna .................. A61F 2/844
623/9

OTHER PUBLICATIONS

Description translation of RU 2410045 (Year: 2011).*
Translation of CN107158536 (Year: 2017).*
Shai et al., "Insertion of a novel T-tube into an intricate subglottic stenosis," Asian Journal of Surgery, vol. 44, Issue 6, Jun. 2021, pp. 877-880, 4 pages.
Shai et al., "Treatment and review of hypopharyngeal stenosis combining complete occlusion" and English translation, Taiwan Medical Journal, 2021, vol. 64, No. 3, pp. 16-20., 13 pages.

* cited by examiner

NON-INVASIVELY AND SAFELY AND QUICKLY SURGICAL TECHNIQUE OF INSERTING T-SHAPED TUBE INTO STENOTIC TRACHEA

BACKGROUND OF THE INVENTION

Field of Invention

The invention relates to a surgical technique, and more particularly to a non-invasively and safely and quickly surgical technique of inserting a T-shaped tube into a stenotic trachea.

Related Art

There are many causes for tracheal stenosis, such as disease, trauma, surgery, etc., and the location of tracheal stenosis will affect the consequence of treatment. Among the different lesions, the most common cause of subglottic stenosis derived from tracheal intubation malfunction or/and sequelae of tracheostomy; treatment of subglottic stenosis is more intricate comparing with lower tracheal stenosis.

In clinical practice, surgical resection and reconstruction are still prime option for curing tracheal stenosis. Specifically, operations of sleeve tracheal resection and reconstruction, or tracheoplasty, laryngotracheotomy combined with T-shaped tube support are all methods to treat subglottic stenosis currently. However, when the patient is deemed unsuitable for surgical resection, alternative methods are chosen for treatment such as laser, dilation, or tracheal stent; patients with obvious subglottic stenosis treated with T-shaped tube insertion often encounter the tricky problem in positioning the upper arm. Although previous experiences have revealed the technique of tackling a traditional rigid bronchoscope to assist inserting a T-shaped tube into the trachea, this surgical procedure is always time-consuming and laborious to manipulate, and maneuvers of the rigid bronchoscope not only requires the aid of an experienced anesthesiologist, but also confront the risk of damage to the patient's vocal cords and trachea.

SUMMARY OF THE INVENTION

A main object of the invention is to provide a non-invasively and safely and quickly surgical technique of inserting a T-shaped tube into a stenotic trachea capable of replacing a rigid bronchoscope with a fiber bronchoscope, in which the T-shaped tube can be inserted into a patient's trachea without additional surgical wound, adopting with the correctable and removable merits of the T-shaped tube as a tracheal stent; especially in patients with moderate stroke receive adequate T-tube insertion could speak to enhance vocal cords mobilization and improve swallowing function, thus, it can maintain the patient's voice or reduce the risk of aspiration of the swallowing. Consequently, it can improve the post-operative quality of life and strengthen the patient's willingness to receive further beneficial treatment and rehabilitation.

Another object of the invention is to provide a non-invasively and safely and quickly surgical technique of inserting a T-shaped tube into a severe tracheal stenosis including even complete trachea obstruction with a tracheostoma in situ. The merit of innovated technique for T-shaped tube insertion can be readily snapped into a patient's trachea without additional surgical wound incision, which can effectively obliterate the conventional drawback of treatment of tracheal stenosis.

Yet another object of the invention is to provide a non-invasively and safely and quickly surgical technique of inserting a T-shaped tube into a stenotic trachea, it can streamline the treatment procedure, shorten the operation time, and reduce a patient's risk of anesthesia, this can be even applied to patient assessment of a high risk for surgery.

In order to achieve the above-mentioned objects, the invention discloses a non-invasively and safely and quickly surgical technique of inserting a T-shaped tube into a stenotic trachea without additional surgical incision for applying to patients with an existing tracheostoma, even when patients were diagnosed as unsuitable for traditional resection and reconstruction.

In one embodiment of the invention, the disclosed surgical method, non-invasively and safely and quickly, inserting the T-shaped tube into the stenotic trachea, comprise steps as followed: (a) adopting a guide tube, following inserting the guide tube into the T-shaped tube, protruding two ends of the guide tube respectively from the side arm to the lower arm of the T-shaped tube; (b) clamping a lower arm end of the T-shaped tube by a clamping tool to make the lower arm end of the T-shaped tube to enter distal trachea through the tracheostoma, so that the lower arm of the T-shaped tube combined with the guide tube entering the distal trachea; then pushing an upper arm end of the T-shaped tube by the clamping tool to make the upper arm end of the T-shaped tube to snap into the trachea through the tracheostoma, so that the upper arm of the T-shaped tube residing the proximal trachea; and inner fixing the side arm of the T-shaped tube into the location of tracheostoma.

Wherein, the guide tube is a sputum suction tube, preferably a sputum suction tube with a diameter of No. 14 (14 Fr).

Wherein, the guide tube protrudes 6-12 cm from a lower arm port of the T-shaped tube, preferably protruding about 10 cm from the lower arm port of the T-shaped tube.

Since each patient's tracheal stenosis is different, the patient's tracheal status should be confirmed before the T-shaped tube insertion, and tracheal dilation should be performed according to the patient's advanced grade of tracheal stenosis, and the procedures ensured the T-shaped tube is capable of inserting the proximal trachea readily.

In one embodiment of the invention, the disclosed surgical method, non-invasively and safely and quickly inserting the T-shaped tube into the stenotic trachea, comprise further step a1: evaluating pathological changes of the trachea with a rigid laryngoscope and a fiber bronchoscope. Wherein, classification of the tracheal stenosis with various pathological changes were defined as followed: grade I is that an obstructed area of the trachea is less than or equal to 50%; grade II is that an obstructed area of the trachea is between 51% and 70%; grade III is that an obstructed area of the trachea is between 71% and 99%; and grade IV is complete (100%) obstruction of the trachea.

When the tracheal obstruction is classified as grade II to IV and require tracheal dilation procedures, involving with a baker dilator, or laser, and last a fiber bronchoscope inner-guiding an endotracheal tube; these ensure that adequate space in the trachea for accommodating the endotracheal tube, followed by the endotracheal tube sleeved on the fiber bronchoscope and inserted into the trachea via patient's mouth. Which confirm the tracheal situation and verify the fiber bronchoscope can be protruding out the tracheostoma.

In order to smoothly insert the T-shaped tube into the trachea of the patient with subglottic stenosis, in the step a, using a guide belt to guide the upper arm of the T-shaped tube to readily snap the proximal trachea. Specifically, in the step a, grasping one end of the guide belt from the tracheostoma back to protrude out patient's mouth, and following the guide belt passing through the upper arm and the side arm of the T-shaped tube and protruding to both ends, thereby, in the step b, by applying a pulling force to the mouth end of the guide belt, pushing the upper arm of the T-shaped tube into the trachea along a path of the guide belt.

Wherein, the upper arm of the T-shaped tube is inserted into a part where tracheal obstruction is diagnosed in the step a1 so as to achieve an efficacy for treatment of tracheal stenosis.

Wherein, the guide belt is a belt with almost no elastic coefficient, such as a tracheostomy tube binding band.

Wherein, in order to prevent the guide belt detaching from the T-shaped tube in refractory subglottic stenosis, a suture is used to unite the upper arm of the T-shaped tube and the guide belt, which means that the suture penetrates through the guide belt and two opposite wall of an end portion of the upper arm of the T-shaped tube, and two ends of the suture are knotted together so that an upper arm port of the T-shaped tube is reduced to a flat opening with 50% of an original cross-sectional area. After the T-shaped-tube is inserted into the proximal trachea, the suture is removed perorally by endoscopic knife.

In one embodiment of the invention, enabling the T-shaped tube to slide into the trachea is achieved by reducing a friction between the T-shaped tube and the trachea, for example, the T-shaped tube is rinsed with saline or/and jelley before placing the T-shaped tube to achieve a purpose of lubrication.

In one embodiment of the invention, in order to be more convenient to apply force to the guide belt, a clamping tool such as KELLY hemostatic forceps is used to clamp the other end of the guide belt so as to fix and pull the guide belt.

In order to facilitate placement of the T-shaped tube and avoid the patient's discomfort, in one embodiment of the invention, an inclination correction of the tracheostoma suitable for the T-shaped tube inserting, that is, an inclination of the tracheostoma and its passage can be adjusted to a right angle by means of fingers or a dilator maneuver.

DETAILED DESCRIPTION OF THE INVENTION

A non-invasively and safely and quickly surgical technique of inserting a T-shaped tube into a stenotic trachea disclosed in the invention is capable of replacing a traditional rigid bronchoscope with a fiber bronchoscope and inserting the T-shaped tube into the existing tracheostoma without an additional surgical wound, so the invention can not only be applied in patients assessment with high risk for surgery, such as stroke, but also the T-shaped tube successfully enters the trachea, an airway can be reformed to treat complex subglottic stenosis, thus, it can maintain the patient's speaking ability or reduce the risk of aspiration of the swallowing.

Further, in the non-invasively and safely and quickly surgical technique of inserting the T-shaped tube into the stenotic trachea disclosed in the invention, according to different conditions of the patient's tracheal stenosis or pathological changes. Through an object such as a sputum suction tube or a tracheostomy tube binding band for guiding the T-shaped tube plus assisting by a flexible fiber bronchoscope; thus, the upper arm and a lower arm of the T-shaped tube can be respectively inserted into the proximal and distal trachea via the tracheostoma. It can acquire an efficacy of safe, quick and reliable treatment.

Figure 1:
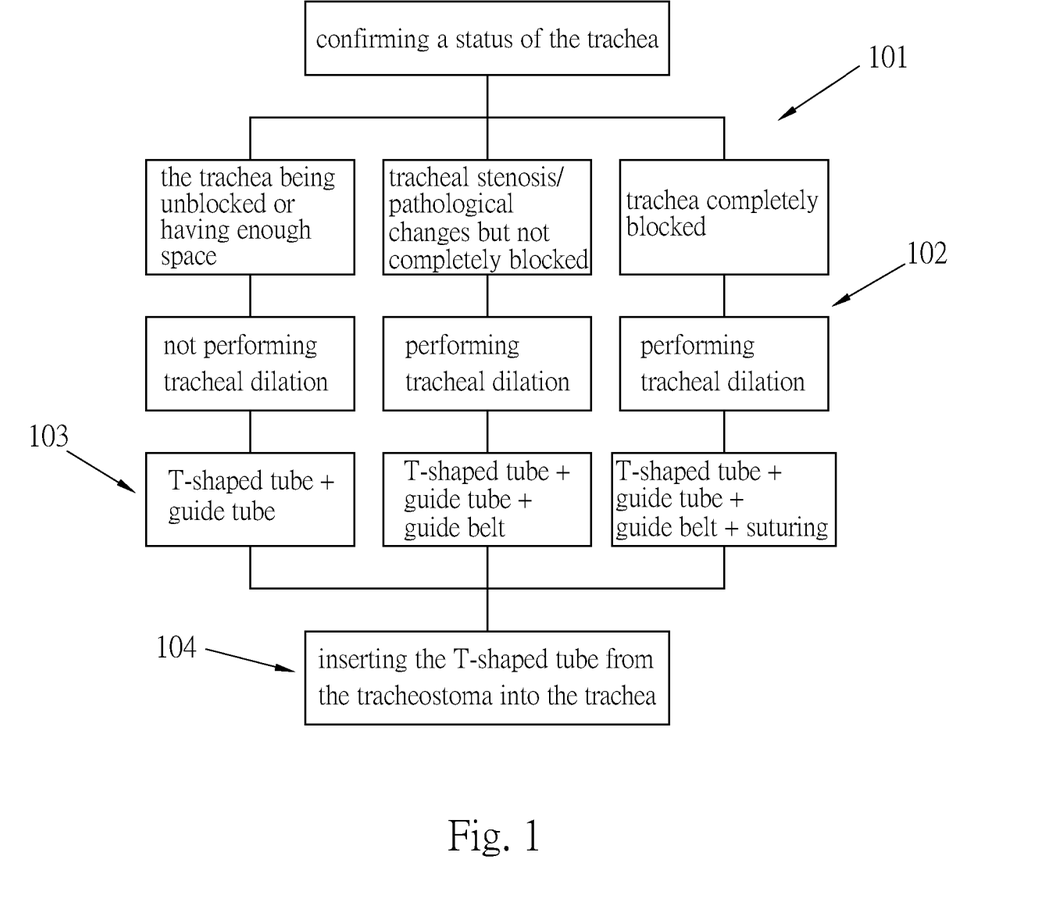
FIG. 1 is a flow chart of a non-invasively and safely and quickly surgical technique of inserting a T-shaped tube into a stenotic trachea disclosed in the invention.

As shown in FIG. 1, the non-invasively and safely and quickly surgical technique of inserting the T-shaped tube into the stenotic trachea disclosed in the invention comprising following steps:

step 101: confirming a status of the patient's trachea using a rigid laryngoscope and a fiber bronchoscope to confirm the trachea being unblocked and determine whether the patient's trachea with adequate space for stenotic trachea;

step 102: determining whether to perform tracheal dilation according to the patient's tracheal status if the patient's trachea being confirmed tracheal stenosis within sufficient space, it is necessary to treat the stenosis by tracheal dilation to ensure that the tracheal space sufficient for inserting a T-shaped tube; if the patient's trachea with adequate space, and tracheal dilation being not required;

step 103: guiding the T-shaped tube according to the degrees of severe tracheal stenosis or pathological changes, guiding the T-shaped tube with different methods to ensure that the upper arm and the lower arm of the T-shaped tube can be respectively inserted in proximal and distal trachea via the tracheostoma; wherein:

when the patient's tracheal status is diagnosed with adequate space, a guide tube is inserted into the T-shaped tube, and two ends of the guide tube are protruded from the side arm and the lower arm of the T-shaped tube respectively; generally speaking, the guide tube protrudes about 6-12 cm from the lower arm port of the T-shaped tube to facilitate guiding the lower arm of the T-shaped tube into distal trachea;

when the patient's trachea is diagnosed as severe tracheal stenosis still with residual lumen, furthermore, a guide belt is helpful to insert the T-shaped tube, and two sides of the guide belt are protruded from both the side arm and the upper arm respectively; in addition to placing the guide tube in the T-shaped tube; a specific surgical procedures are elucidated as follows, the fiber bronchoscope is inserted into the trachea from the mouth of the patient, and is protruded from the tracheostoma, subsequently a tissue slice forcep is protruded from the fiber bronchoscope tip and grasp on one end of the guide belt; pulling the fiber bronchoscope out from an oral cavity, so that the end of the guide belt is protruded from the mouth, and the other end of the guide belt is protruded out the tracheostoma, eventually, the guide belt is passing through the upper arm to the side arm of the T-shaped tube, and protruded from both port of the T-shaped tube;

when the patient's trachea is diagnosed as complete tracheal stenosis or complex subglottic stenosis, thus, a suture is applied to penetrate two opposite tube walls of an upper arm port of the T-shaped tube and the guide belt, and the upper arm port of the T-shaped tube is deformed by knotting two ends of the suture to a flat opening, so that the upper arm of the T-shaped tube can be readily inserted into the proximal trachea; in addition to placing the guide tube and the guide belt in the T-shaped tube as described above; and step 104: inserting the T-shaped tube from the tracheostoma into the trachea after preparation of guiding the T-shaped tube, first guiding the lower arm of the T-shaped tube into distal trachea below the tracheostoma through the guide tube; and then pushing the upper arm of the T-shaped tube into the proximal trachea of the tracheostoma, if the guide belt being disposed in the T-shaped tube, driving the upper arm of the T-shaped tube into the proximal trachea by simultaneously applying a pulling force on the guide belt by mouth end; if the guide belt being not disposed in the T-shaped tube, inserting the upper arm of the T-shaped tube into the proximal trachea directly; in addition, on the occasion of the T-shaped tube being connected to the guide belt with the suture, removing the suture by endoscopic knife. Completion of adequately insert the T-shaped tube into the trachea, and reside the side arm of the T-shaped tube on the tracheostoma with inner fixation of the T-shaped tube.

The term "subglottic stenosis" mentioned in the invention refers to a situation where the trachea at a position below the vocal cords (or called the glottis) is obstructed, resulting in airway stenosis. According to the Cotton-Myer classification system, tracheal stenosis is classified according to a degree of obstructed lumen of the trachea, grade I is that an obstructed area of the trachea is less than or equal to 50%; grade II is that an obstructed area of the trachea is between 51% and 70%; grade III is that an obstructed area of the trachea is between 71% and 99%; and grade IV is complete (100%) obstruction of the trachea. Generally speaking, those with an obstructed area of the trachea of more than 50% will have a symptom of difficulty in breathing during exercise; those with an obstructed area of the trachea of more than 75% will have obvious strider and wheezing at rest.

The term "complex subglottic stenosis" mentioned in the invention refers to patients who have diseases of subglottic stenosis, the length, nature, surface and volume of the lesion were intricate with an obstructed cross-section area of the lumen more than 50%. Such patients are often evaluated as unsuitable for tracheal resection.

The term "pathological changes of the trachea" mentioned in the invention refers to tracheal stenosis of various degrees caused by diseases, injury after intubation, etc., such as under the vocal cords, over-expanded cuff of the endotracheal tube will cause ischemia and ulcer of the tracheal mucosa, subsequent fibrosis and scar tissues will be produced after wound healing and resulting in tracheal stenosis.

The "laryngoscope" disclosed in the invention does not harm the vocal cords, such as curved laryngeal mask airway (LMA), rigid laryngoscope, etc.

The "T-shaped tube" disclosed in the invention is a tube shaped like a T, which can be made of any medically acceptable material, such as silicone rubber.

The "guide tube" disclosed in the invention is a medically acceptable tube. In one embodiment of the invention, the guide tube is a sputum suction tube, and a size of No. 14 is preferred.

The "guide belt" disclosed in the invention is a medically acceptable belt with almost no elasticity. The guide belt is usually a braided belt. In one embodiment of the invention, the guide belt is a tracheostomy tube binding band.

Figure 2:
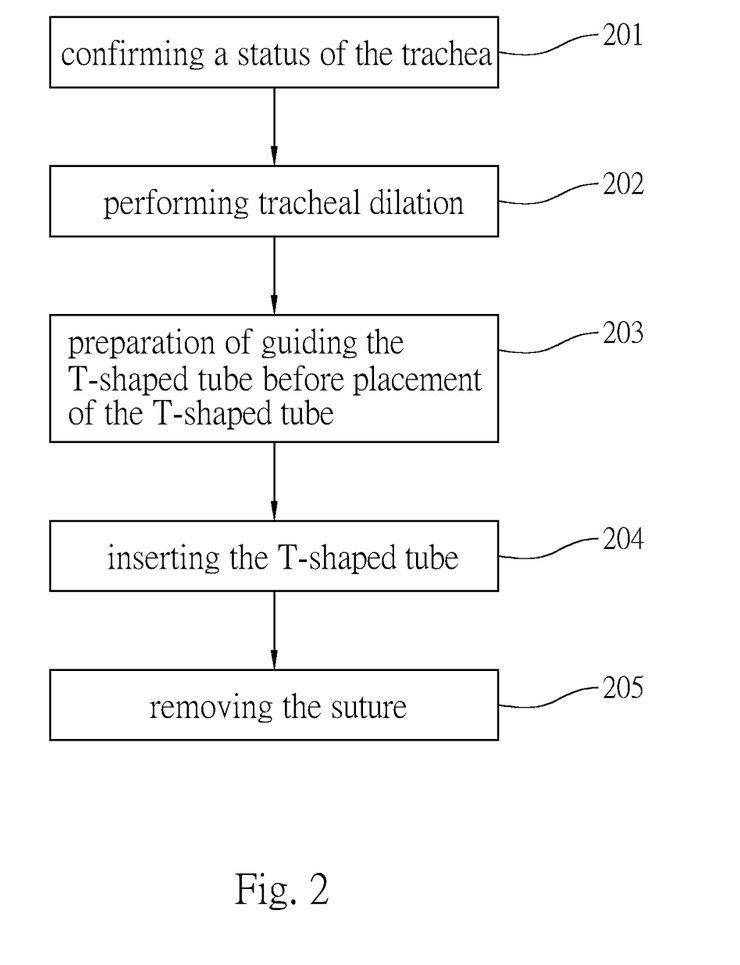
FIG. 2 is a flow chart of the non-invasively and safely and quickly surgical technique of inserting the T-shaped tube into the stenotic trachea disclosed in one embodiment of the invention.
Figure 3:
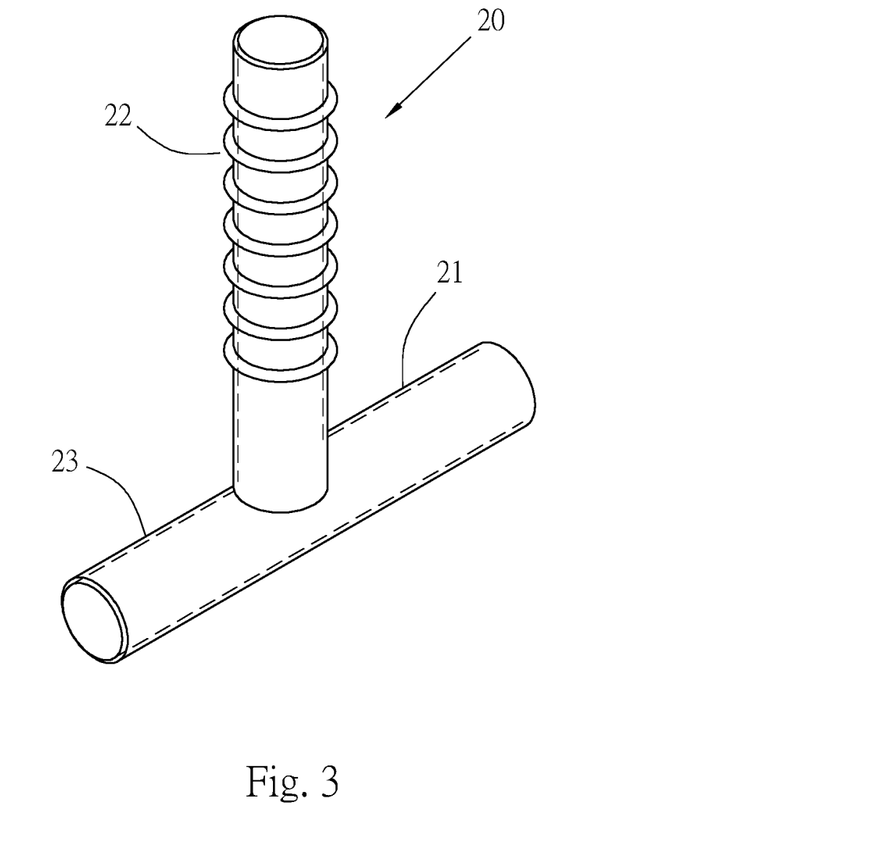
FIG. 3 is a perspective view of the T-shaped tube disclosed in one embodiment of the invention.
Figure 4:
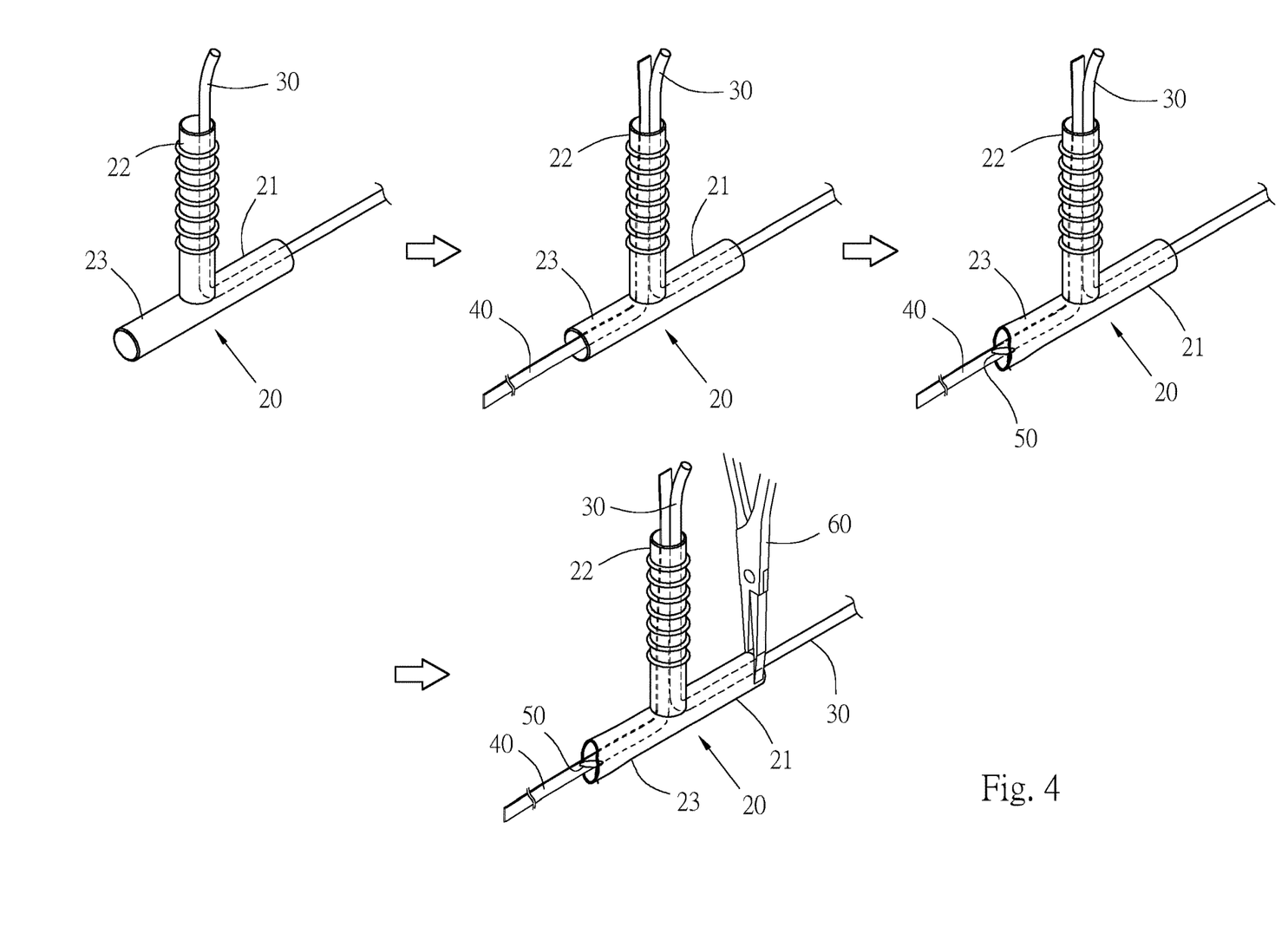
FIG. 4 is a schematic diagram of step 203 in one embodiment of the invention.
Figure 5:
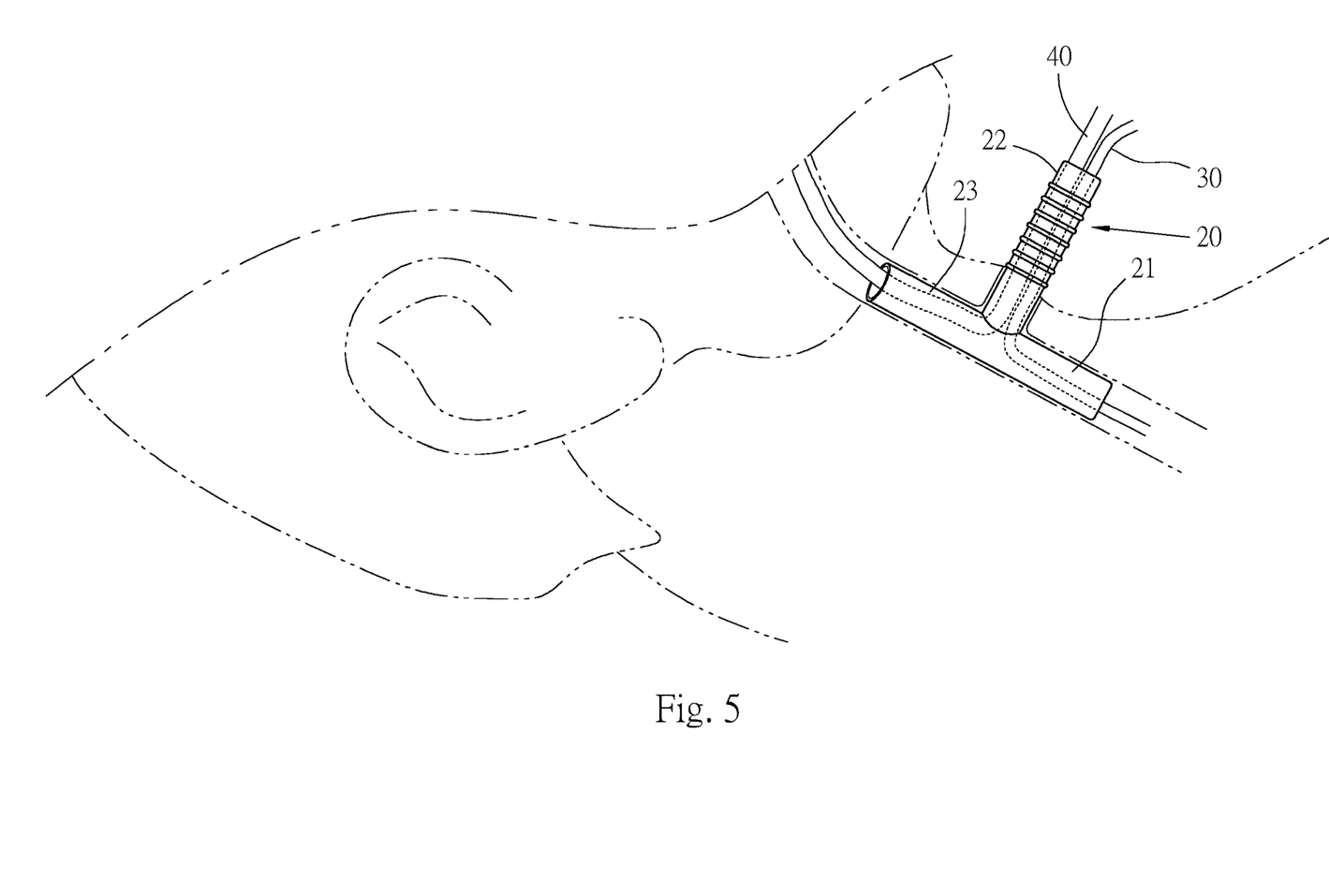
FIG. 5 is a schematic diagram of inserting the T-shaped tube into a trachea of a patient disclosed in one embodiment of the invention.

The non-invasively and safely and quickly surgical technique of inserting the T-shaped tube into the stenotic trachea disclosed in a first embodiment of the invention is used in a patient whose trachea is completely obstructed, and the patient has undergone tracheostomy; for specific details, please refer to the FIGS. 2 to 5, the non-invasively and safely and quickly surgical technique of inserting the T-shaped tube into the stenotic trachea comprising following steps:

step 201: confirming a part of the trachea with pathological changes first, raising the patient's epiglottic cartilage with a fixed rigid laryngoscope to make the glottis clearly visible, and then inserting a fiber bronchoscope into the patient's trachea to confirm an obstructed status of the trachea;

step 202: dilation of the trachea dilating the trachea in different ways, including using baker dilators of different calibers for tracheal dilation, laser resection, and even using a rigid bronchoscope for tracheal shaping, after sleeving an endotracheal tube on the fiber bronchoscope, inserting the endotracheal tube together with the fiber bronchoscope into the trachea to ensure that the trachea being unimpeded and the fiber bronchoscope being capable of entering the trachea perorally and protruding through the tracheostoma;

step 203: preparation of guiding the T-shaped tube before placement of the T-shaped tube measuring a distance between the lesion of the trachea with pathological changes and the tracheostoma, and selecting the appropriate size of T-shaped tube according to the measured distance, if incapable of selecting the T-shaped tube corresponding to the distance, adjusting a size of each of the arms of the T-shaped tube by trimming or polishing;

referring to FIGS. 3 to 4, inserting a sputum suction tube 30 into a lower arm 21 and a side arm 22 of a T-shaped tube 20, and protruding two ends of the sputum suction tube 30 from the lower arm 21 and the side arm 22 of the T-shaped tube 20 respectively, wherein one end of the sputum suction tube 30 protrudes about 10 cm from a port of the lower arm 21; and using a clamping tool 60, such as KELLY hemostatic forceps to clamp the lower arm 21 and the sputum suction tube 30 located inside the lower arm 21 at the same time;

then clamping one end of a tracheostomy tube fixing band 40 with the fiber bronchoscope from the tracheostoma of the patient along with the fiber bronchoscope and protruding from the mouth, so that the tracheostomy tube fixing band 40 entering the trachea; after detaching the end of the tracheostomy tube fixing band 40 from the fiber bronchoscope, the tracheostomy tube fixing band 40 entering the T-shaped tube 20 from a port of an upper arm 23 of the T-shaped tube 20 and protruding a predetermined length from a port of the side arm 22; and then a suture 50 radially penetrating two tube walls of the port of the upper arm 23 of the T-shaped tube 20 and the tracheostomy tube fixing band 40 located in the upper arm 23, making two ends of the suture 50 close to each other and combining the two ends to cause the port of the upper arm 23 of the T-shaped tube 20 to change from a circular opening to a 50% flat opening to restrict the tracheostomy tube fixing band 40 from detaching from the T-shaped tube;

step 204: inserting the T-shaped tube after lubricating the inside and outside of the T-shaped tube 20 with physiological saline or jelley, first using the clamping tool 60 to place one end of the sputum suction tube 30 exposed from the lower arm 21 of the T-shaped tube 20 into the tracheostoma and moving the sputum suction tube 30 toward the distal trachea of the tracheostoma, thereby guiding the lower arm 21 of the T-shaped tube 20 into the distal trachea of the tracheostoma; then making the upper arm 23 of the T-shaped tube 20 to pass through the tracheostoma and moving the upper arm 23 of the T-shaped tube 20 toward the proximal trachea of the tracheostoma, at the same time applying an external force to pull another end of the tracheostomy tube fixing band 40 to drive the upper arm 23 of the T-shaped tube 20 to move along the trachea toward the patient's mouth; when the upper arm 23 and the lower arm 21 of the T-shaped tube 20 entering the proximal trachea of the tracheostoma and the distal trachea of tracheostoma respectively, the side arm 22 of the T-shaped tube 20 being inner fixed the tracheostoma;

wherein, in order to enable the upper arm 23 and the lower arm 21 of the T-shaped tube 20 to enter the trachea readily, an angle of the tracheostoma needs to be adjusted so that it appears approximately vertical before the T-shaped tube 20 is inserted into the trachea; and step 205: removing the suture after confirming a placement position of the T-shaped tube 20 with the laryngoscope and the fiber bronchoscope, removing the suture 50.

It can be known from the above description that the non-invasively and safely and quickly surgical technique of inserting the T-shaped tube into the stenotic trachea disclosed in the invention has the following innovations and advantages:

firstly, the T-shaped tube can be inserted through the patient's existing tracheostoma without additional neck incisions, which not only shortens the operation time, but also reduces the recovery time;

secondly, the fiber bronchoscope is used to replace the rigid bronchoscope during the operation, which not only reduces the complexity of the procedures, but also does not harm the patient's vocal cord and trachea, after the operation, it will not affect the patient's voice and phonation; and thirdly, the surgical method disclosed in the invention can be applied to patients assessmented as unsuitable for resection, and can also be even applied to patients with complete subglottic and trachea obstruction, which is very beneficial for the treatment and enhancing prognosis of tracheal stenosis.

The above-mentioned embodiments are merely used to illustrate the technical ideas and features of the invention, with an object to enable any person having ordinary skill in the art to understand the technical content of the invention and implement it accordingly, the embodiments are not intended to limit the claims of the invention, and all other equivalent changes and modifications completed based on the technical means disclosed in the invention should be included in the claims covered by the invention.

What is claimed is:

1. A non-invasively and safely and quickly surgical technique of inserting a T-shaped tube into a stenotic trachea comprising steps as followed:

(a) adopting a guide tube and inserting the guide tube into the T-shaped tube, protruding two ends of the guide tube respectively from a side arm and a lower arm of the T-shaped tube;

after the step (a), (a1) confirming a status of the trachea, classifying according to an obstructed area of the trachea, wherein grade I is that an obstructed area of the trachea is less than or equal to 50%; grade II is that an obstructed area of the trachea is between 51% and 70%; grade III is that an obstructed area of the trachea is between 71% and 99%; and grade IV is complete (100%) obstruction of the trachea; when the status of the trachea is classified to grade II~IV, performing a tracheal dilation procedure for the patient's narrowed trachea; and (b) clamping a lower arm end of the T-shaped tube with a clamping tool to make the lower arm end of the T-shaped tube to enter a distal trachea through a tracheostoma, so that the lower arm of the T-shaped tube and one of the ends of the guide tube entering the distal trachea; then clamping an upper arm end of the T-shaped tube with the clamping tool to make the upper arm end of the T-shaped tube to enter a proximal trachea through the tracheostoma, so that the upper arm of the T-shaped tube entering the proximal trachea; and inner fixing the side arm of the T-shaped tube into the tracheostoma;

wherein when the step (a1) confirms that the status of the trachea of the patient is classified to grade II~IV, the step (a) further comprises a suitable guide belt, putting the guide belt into the trachea, protruding out one end of the guide belt from the tracheostoma to the patient's mouth;

subsequently, the guide belt is passing through the upper arm and the side arm of the T-shaped tube;

in the step (b), by applying a pulling force to the mouth end of the guide belt, pushing the upper arm of the T-shaped tube into the proximal trachea.

2. The non-invasively and safely and quickly surgical technique of inserting the T-shaped tube into the stenotic trachea as claimed in claim 1, wherein in the step (a1), using a rigid laryngoscope and a fiber bronchoscope to confirm the virtual status of the trachea.

3. The non-invasively and safely and quickly surgical technique of inserting the T-shaped tube into the stenotic trachea as claimed in claim 1, wherein the tracheal dilation procedure comprises first dilating the trachea with a laser or a dilator, following inserting a fiber bronchoscope into an endotracheal tube, and the endotracheal tube entering the trachea from mouth of the patient for final dilatation and ventilation.

4. The non-invasively and safely and quickly surgical technique of inserting the T-shaped tube into the stenotic trachea as claimed in claim 1, wherein when the step (a1) confirms that the status of the trachea is classified to grade III, the step (a) further consist of a suture stitch to unite the upper arm of the T-shaped tube and the guide belt to prevent the guide belt from detaching.

5. The non-invasively and safely and quickly surgical technique of inserting the T-shaped tube into the stenotic trachea as claimed in claim 4, wherein in the step (a), using the suture to penetrate the upper arm of the T-shaped tube and the guide belt, and an upper arm port of the T-shaped tube approximate to a 50% flat opening by knotting two ends of the suture.

6. The non-invasively and safely and quickly surgical technique of inserting the T-shaped tube into the stenotic trachea as claimed in claim 4, further comprising a step (c) following the step (b);

(c) removing the suture stitch.

7. The non-invasively and safely and quickly surgical technique of inserting the T-shaped tube into the stenotic trachea as claimed in claim 1, wherein the guide belt is a tracheostomy tube binding band.

8. The non-invasively and safely and quickly surgical technique of inserting the T-shaped tube into the stenotic trachea as claimed in claim 1, wherein the upper arm of the T-shaped tube is inserted into a part where tracheal obstruction is diagnosed in the step (a1).

9. The non-invasively and safely and quickly surgical technique of inserting the T-shaped tube into the stenotic trachea as claimed in claim 1, wherein the guide tube is a sputum suction tube.

10. The non-invasively and safely and quickly surgical technique of inserting the T-shaped tube into the stenotic trachea as claimed in claim 1, wherein in the step (a), the guide tube protrudes 6-12 cm from a lower arm port of the T-shaped tube.

11. The non-invasively and safely and quickly surgical technique of inserting the T-shaped tube into the stenotic trachea as claimed in claim 1, wherein in the step (b), the T-shaped tube is lubricated before the T-shaped tube inserts into the trachea.

* * * * *